United States Patent [19]

Dornhagen et al.

[11] Patent Number: 4,988,685
[45] Date of Patent: Jan. 29, 1991

[54] CEPHALOSPORINS DERIVATIVES

[75] Inventors: Jürgen Dornhagen, Eimeldingen; Rolf Angerbauer; Karl G. Metzger, both of Wuppertal; Hans-Joachim Zeiler, Velbert, all of Fed. Rep. of Germany

[73] Assignee: Bayer Aktiengesellschaft, Leverkusen, Fed. Rep. of Germany

[21] Appl. No.: 464,662

[22] Filed: Jan. 11, 1990

Related U.S. Application Data

[63] Continuation of Ser. No. 170,523, Mar. 18, 1988, abandoned.

[30] Foreign Application Priority Data

Apr. 3, 1987 [DE] Fed. Rep. of Germany ....... 3711343

[51] Int. Cl.$^5$ ................. C07D 501/56; A61K 31/545
[52] U.S. Cl. ..................................... 514/202; 540/222
[58] Field of Search ..................... 540/227, 222, 225; 514/202

[56] References Cited

U.S. PATENT DOCUMENTS 4,616,081 10/1986 Nishikido et al. ................. 540/225
4,748,171 5/1988 Yamauchi et al. ................. 540/222

FOREIGN PATENT DOCUMENTS 3506159 2/1985 Fed. Rep. of Germany .

OTHER PUBLICATIONS

Chemical Abstracts, vol. 107, No. 15, Oct. 12, 1987, p. 704.

*Primary Examiner*—Nicholas S. Rizzo
*Attorney, Agent, or Firm*—Sprung Horn Kramer & Woods

[57] ABSTRACT

Novel cephalosporins of the formula

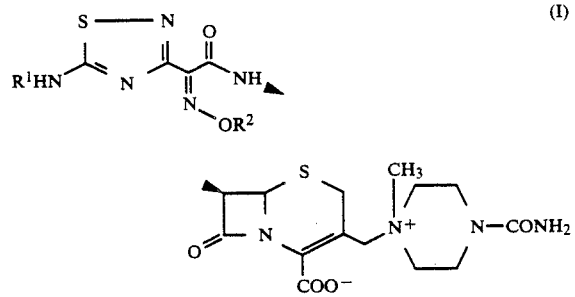

in which
R$^1$ represents hydrogen or an amino-protecting group and
R$^2$ represents alkyl, cycloalkyl or alkenyl.

14 Claims, No Drawings

CEPHALOSPORINS DERIVATIVES

This application is a continuation, of application Ser. No. 170,523, filed 3/18/88 now abandoned.

The invention relates to cephalosporin derivatives, a process for their preparation, and their use as medicaments, in particular, in antibacterial therapy.

Cephalosporins which contain as acyl side chain a 2-(2-aminothiazol-4-yl)-2-alkoxyiminoacetic acid radical and carry in the 3-position a 4-aminocarbonyl-1-methylpiperazinium)methyl radical have been disclosed in U.S. Ser. No. 083,766, filed Aug. 10, 1987, now pending.

The present invention relates to new cephalosporin derivatives of the general formula (I)

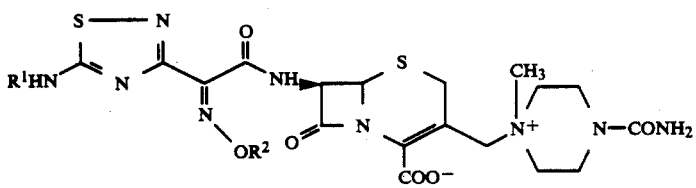

in which
R¹ represents hydrogen or an amino-protecting group,
and
R² represents alkyl, cycloalkyl, or alkenyl.

In general, alkyl represents a straight-chain or branched hydrocarbon radical having 1 to 12 carbon atoms. Lower alkyl having 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

In general, alkenyl represents a straight-chain or branched hydrocarbon radical having 2 to 12 carbon atoms and one or more, preferably one or two, double bonds. The lower alkyl radical having about 2 to about 6 carbon atoms and one double bond is preferred. An alkenyl radical having 2 to 4 carbon atoms and one double bond is particularly preferred. Examples which may be mentioned are alkyl, propenyl, isopropenyl, butenyl, isobutenyl, pentenyl, isopentenyl, hexenyl, isohexenyl, heptenyl, isoheptenyl, octenyl and isooctenyl. In general, cycloalkyl represents a radical having up to 12 carbon atoms.

In the context of the abovementioned definition, amino-protecting group generally represents a protecting group which is conventional in β-lactam chemistry from the series comprising: 4-methoxyphenyl, 4-methoxymethyloxyphenyl, 4-[(2-methoxyethoxy)methyloxy]phenyl, 3,4-dimethoxyphenyl, benzyl, 2-nitrobenzyl, 4-nitrobenzyl, 4-methoxybenzyl, 2,4-dimethoxybenzyl, 3,4-dimethoxybenzyl, 2,4,6-trimethoxybenzyl, vinyl, allyl, tert-butoxycarbonyl, benzyloxycarbonyl, 2-nitrobenzyloxycarbonyl, 4-nitrobenzyloxycarbonyl, formyl, acetyl, chloroacetyl, trichloroacetyl, trifluoroacetyl, benzoyl, methoxycarbonyl, allyloxycarbonyl, 2,4-dimethoxybenzyloxycarbonyl, 2,2-diethoxyethyl, methoxycarbonylmethyl, tert-butoxycarbonylmethyl, allyloxymethyl, benzoylmethyl, bis-(4-methoxyphenyl)methyl, methoxymethyl, methylthiomethyl, methoxyethoxymethyl, 2-(methylthiomethoxy)ethoxycarbonyl, 2-hydroxy-2-phenylmethyl, methoxy-(4-methoxyphenyl)methyl, trimethyl-, triethyl and tri- phenylsilyl, tert-butyl-dimethylsilyl, tert-butyldiphenylsilyl and [2-(trimethylsilyl)ethoxy]-methyl.

Preferred compounds of the general formula (I) are those in which
R¹ represents hydrogen or acetyl
and
R² represents straight-chain or branched alkyl having up to 8 carbon atoms or represents cyclopropyl, cyclopentyl or cyclohexyl, or represents straight-chain or branched alkenyl having up to 8 carbon atoms and one or two double bonds.

Particularly preferred compounds of the general formula (I) are those in which
R¹ represents hydrogen
and
R² represents straight-chain or branched alkyl having up to 6 carbon atoms, cyclopentyl, cyclohexyl, or straight-chain or branched alkenyl having up to 4 carbon atoms and one double bond.

Of the compounds of the general formula (I) according to the invention, it is possible for several isomers to be produced which are all antibiotically active and, if desired, can be resolved by chromatography or crystallization.

The compounds of the general formula (I) are obtained in a process in which carboxylic acids of the general formula (II)

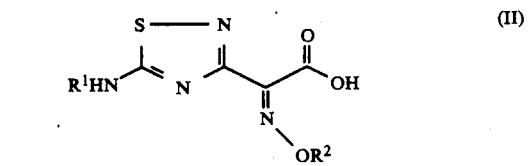

in which
R¹ and R² have the abovementioned meaning, after activation of the carboxy group by conversion into a mixed anhydride, for example using ethyl chloroformate or methanesulphonyl chloride, or by conversion into the acyl halide, or by conversion into an activated ester, for example using N-hydroxybenzotriazole and cyclohexylcarbodiimide, are reacted with the β-lactam compound of the formula (III),

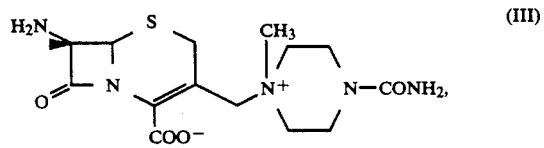

the protecting groups are then removed, if appropriate, and the desired salts are prepared or the free betaines are prepared from the salts.

A large number of methods which are known from cephalosporin or penicillin chemistry can be used for coupling carboxylic acids (II) to the β-lactam compound (III). It has proven advantageous to activate the carboxylic acids of the general formula (II) without an aminoprotecting group and then to couple it to the β-lactam compound of the formula (III), which has been dissolved as salts with an amine.

Activation using sulphonic acid derivatives of the general formula (IV) to give anhydrides of the general formula (V), as illustrated by the following reaction equation, is particularly advantageous:

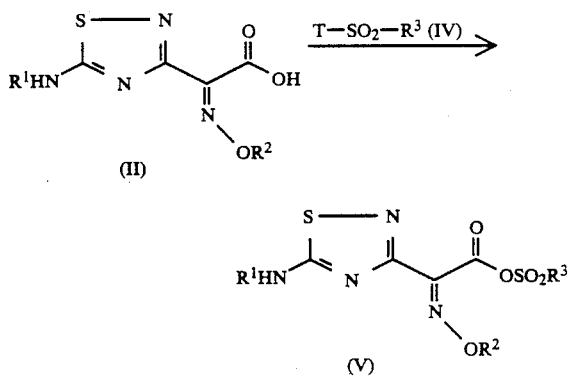

(II)

(V)

In the formula (IV) or (V) in this equation,

T represents the $R^3$—$SO_2$—O— radical or halogen and $R^3$ represents alkyl having up to 10 carbon atoms which is optionally substituted by fluorine, chlorine, cyano, alkyl, alkoxycarbonyl, alkoxy or alkyl in each case having up to 4 carbon atoms, or phenyl which is optionally substituted by fluorine, chlorine, bromine, cyano, alkyl, alkoxy, alkylthio, alkoxycarbonyl in each case having up to 4 carbon atoms, nitro, trifluoromethyl or phenyl.

If $R^3$ is substituted, 1 to 3 substituents are preferably present, particularly preferably the abovementioned.

$R^3$ is very particularly preferably a methyl or p-tolyl radical.

The mixed anhydrides of the general formula (V) are prepared by dissolving the carboxylic acids of the general formula (II) and 1 to 1.4 equivalents of an amine in a solvent and allowing to react with 1 to 1.2 equivalents of a sulphonic acid derivative of the formula (IV).

Suitably solvents are all solvents which do not react under the reaction conditions. These preferably include ethers such as, for example, diethyl ether, dioxane or tetrahydrofuran, or chlorinated hydrocarbons, such as methylene chloride, chloroform or tetrachloromethane, or amides, such as dimethylformamide or hexamethylphosphoric triamide, or acetonitrile or acetone. It is likewise possible to employ mixtures of the solvents mentioned.

Suitable amines are tertiary amines, such as, for example, triethylamine, ethyl-diisopropylamine or tributylamine, but also sterically hindered secondary amines, such as, for example, diisopropylamine. It is likewise possible to employ mixtures of the amines mentioned.

The reactions can be carried out at temperatures between −80° C. and room temperature. The activation is advantageously carried out using methanesulphonyl chloride in dimethylformamide at −40° C. to −60° C. within 0.2 to 24 hours, preferably 0.5 to 5 hours.

To dissolve the β-lactam compound of the formula (III), the solvents mentioned in the preparation of compounds of the formula (V), or water can be used, and the base used can be the amines mentioned there.

Activation of the carboxylic acids of the general formula (II) by conversion into an activated ester, for example using N-hydroxysuccinimide and dicyclohexylcarbodiimide or using 1-hydroxybenzotriazole and dicyclohexylcarbodiimide, is also particularly advantageous.

Suitable solvents in this process are all solvents which are also suitable for the preparation of anhydrides of the general formula (V) and have already been listed there.

The reactions can be carried out at temperatures between −30° C. and +100° C. In an advantageous process, the activation is carried out using 1-hydroxybenzotriazole and dicyclohexylcarbodiimide in dimethylformamide at room temperature for 2 to 6 hours, the precipitated dicyclohexylurea is then filtered off under suction, and the activated ester is reacted with the β-lactam compound of the formula (III) in the form of a solution of its amine salt within 2 to 24 hours. To dissolve the β-lactam compound of the formula (III), the solvents mentioned in the preparation of the compounds of the formula (V) can be used, and the base used can be the amines mentioned there.

The β-lactam compound of the formula (III) is disclosed in U.S. Ser. No. 083,766, filed Aug. 10, 1987, now pending.

The compounds of the general formula (II) are known or can be prepared by known methods [GB-2,094,794; DE-A-3,512,225].

As an alternative to the process described above, the substances of the general formula (I) according to the invention can also be prepared in a process in which esters of the general formula (VI)

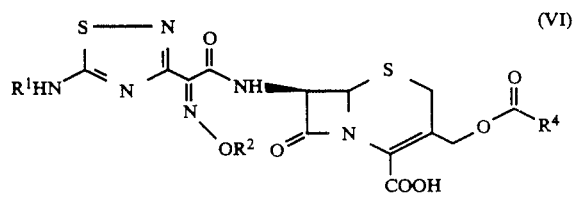

(VI)

in which $R^1$ and $R^2$ have the abovementioned meaning and $R^4$ represents optionally substituted alkyl or aryl, preferably methyl, ethyl, propyl, chloromethyl, dichloromethyl, trichloromethyl, trifluoromethyl or phenyl, or particularly preferably represents a methyl group, are silylated, the silyl compound of the general formula (VII)

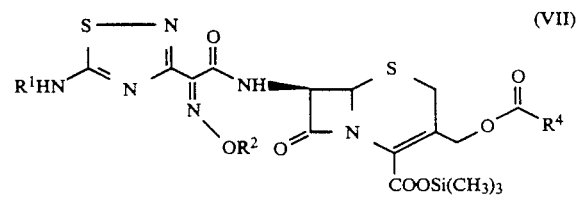

(VII)

in which $R^1$, $R^2$ and $R^4$ have the abovementioned meaning, are converted into the iodomethyl compounds of the general formula (VIII)

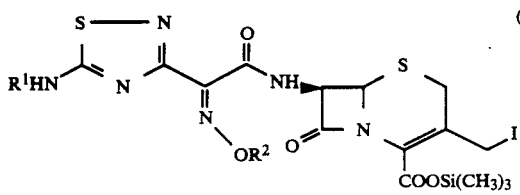

in which $R^1$ and $R^2$ have the abovementioned meaning, and these are subsequently reacted with 1-aminocarbonyl-methylpiperazine of the formula (IX)

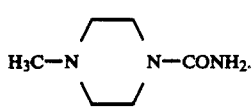

(TMCS), hexamethyldi-silazane (HMDS), N,O-bis(-trimethylsilyl)-acetamide (BSA), N,O-bis(trimethylsilyl)-trifluoroacetamide (BSTFA), N-methyl-N-trimethylsilylacetamide (MSA), N-methyl-N-trimethylsilyl-trifluoroacetamide (MSTFA), 1,3-bis(trimethylsilyl)urea or trimethylsilyl trifluoromethanesulphonate. It is also possible to employ a mixture of several silylating agents in this process.

The silylation is generally carried out in a temperature range from −30° C. to +70° C., preferably from −10° C. to +10° C., within 5 to 30 minutes. In an advantageous fashion, an excess of up to ten-fold of the silylating agent is employed, preferably a two- to five-fold excess.

The solution of the trimethylsilyl ester of the formula (VII) thus obtained is preferably reacted with 3 to 4 equivalents of a trialkylsilyl iodide, particularly preferably trimethylsilyl iodide, within 15 minutes to 2 hours, preferably within 30 minutes to 1 hour, in a temperature range from −40° C. to +30° C. to give compounds of the general formula (VIII).

The compounds of the formula (VIII) are advantageously not isolated, but are reacted directly without

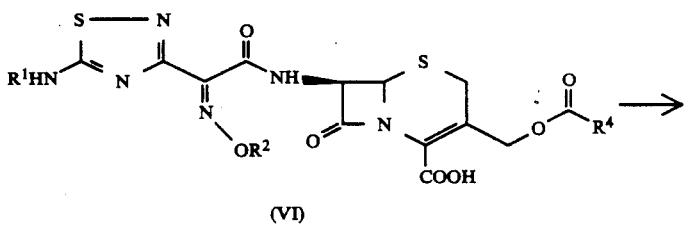

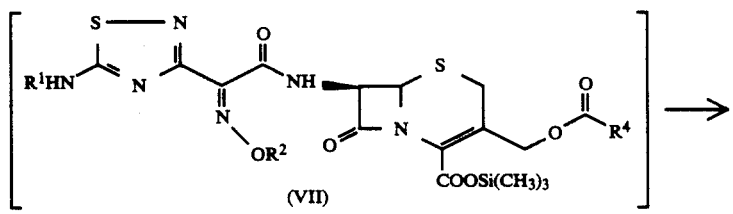

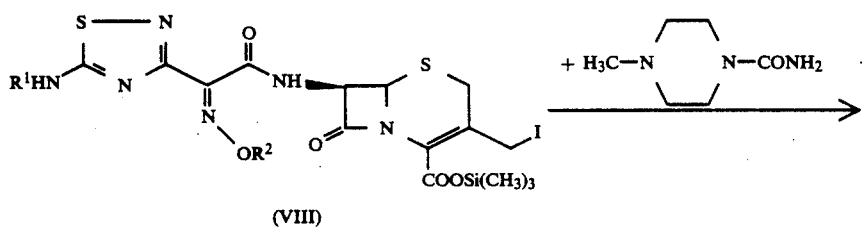

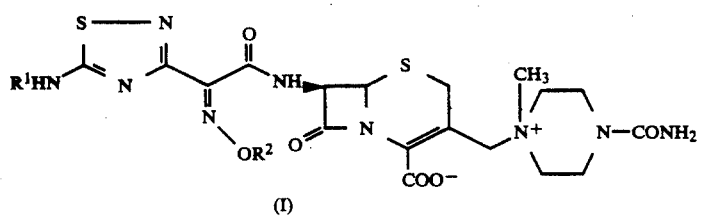

To carry out this process, the starting compounds of the general formula (VI) are suspended in a suitable organic solvent and dissolved by silylation to give the silyl esters (VIII). Particularly suitable organic solvents are chlorinated hydrocarbons, such as, for example, methylene chloride, chloroform or tetrachloroethane. The silylation is carried out using a conventional silylating agent, such as, for example, trimethylchlorosilane purification with 1-aminocarbonyl-4-methylpiperazine of the formula (IX).

The compounds according to the invention are active against a very broad spectrum of microorganisms. They can be used to combat Gram-negative and Gram-positive bacteria and bacteria-like microorganisms and to prevent, ameliorate and/or heal disorders caused by these pathogens.

The compounds according to the invention are particularly active against bacteria and bacteria-like microorganisms. They are therefore particularly suitable for the prophylaxis and chemotherapy of local and systemic infections, caused by these pathogens, in human medicine and veterinary medicine.

For example, local and/or systemic disorders caused by the following pathogens or by mixtures of the following pathogens can be treated and/or prevented:

Gram-positive cocci, for example Staphylococci (*Staph. aureus* and *Staph. epidermidis*) and Streptococci (*Strept. agalactiae, Strept. faecalis, Strept. pneumoniae* and *Strept. pyogenes*); Gram-negative cocci (*Neisseria gonorrhoeae*) and Gram-negative bacilli, such as Enterobacteriaceae, for example *Escherichia coli, Haemophilus influenzae,* Citrobacter (*Citrob. freundii* and *Citrob. divernis*), Salmonella and Shigella; furthermore Klebsiellae (*Klebs. pneumoniae* and *Klebs. oxytoca*), Enterobacter (*Ent. aerogenes* and *Ent. agglomerans*), Hafnia, Serratia (*Serr. marcescens*), Proteus (*Pr. mirabilis, Pr. rettgeri* and *Pr. vulgaris*), Providencia, Yersinia and the Acinetobacter genus. In addition, the antibacterial spectrum covers the genus Pseudomonas (*Ps. aeruginosa* and *Ps. maltophilia* and also strictly anaerobic bacteria, such as, for example, *Bacteroides fragilis*, representatives of the *Peptococcus genus,* Peptostreptococcus and the *Clostridium genus;* furthermore Mycoplasma (*M. pneumoniae, M. hominis* and *M. urealyticum*) and Mycobacteria, for example *Mycobacterium tuberculosis.*

The above list of pathogens is purely illustrative and is in no way to be interpreted as restrictive. The following may be mentioned as examples of illnesses which can be caused by the pathogens mentioned or by mixed infections and can be prevented, ameliorated or healed by the compounds according to the invention:

Infectious diseases in humans, such as, for example, otitis, pharyngitis, pneumonia, peritonitis, pyelonephritis, cystitis, endocarditis, systemic infections, bronchitis (acute and chronic), septic infections, disorders of the upper respiratory tracts, diffuse panbronchiolitis, pulmonary emphysema, dysentery, enteritis, liver abscesses, urethritis, prostatitis, epididymitis, gastro-intestinal infections, bone and joint infections, cystic fibrosis, skin infections, postoperative wound infections, abscesses, phlegmon, wound infections, infected burns, burn wounds, oral infections, infections after dental operations, osteomyelitis, septic arthritis, cholecystitis, peritonitis with appendicitis, cholangitis, intraabdominal abscesses, pancreatitis, sinusitis, mastoiditis, mastitis, tonsillitis, typhoid, meningitis and infections of the nervous system, salpingitis, endometritis, genital infections, pelveoperitonitis and eye infections.

Apart from in humans, bacterial infections can also be treated in other species. Examples which may be mentioned are:

Pig: coli-diarrhoea, enterotoxaemia, sepsis, dysentery, salmonellosis, metritis-mastitis-agalactiae syndrome and mastitis;

Ruminants (cattle, sheep and goat): diarrhoea, sepsis, bronchopneumonia, salmonellosis, pasteurellosis, mycoplasmosis and genital infections;

Horse: bronchopneumonia, joint-ill, puerperal and postpuerperal infections, and salmonellosis;

Dog and cat: bronchopneumonia, diarrhoea, dermatitis, otitis, urinary tract infections and prostatitis;

Poultry (chicken, turkey, quail, dove, cage birds and others): mycoplasmosis, E. coli infections, chronic respiratory tract disorders, salmonellosis, pasteurellosis and psittacosis.

Bacterial infections in the breeding and keeping of productive and ornamental fish can likewise be treated, the antibacterial spectrum extending beyond the previously mentioned pathogens to further pathogens, such as, for example, Pasteurella, Brucella, Campylobacter, Listeria, Erysipelothrix, Corynebacteria, Borellia, Treponema, Nocardia, Rickettsia, Yersinia.

The present invention includes pharmaceutical preparations which, in addition to non-toxic, inert pharmaceutically suitable excipients, contain one or more compounds according to the invention or which comprise one or more active compounds according to the invention, and processes for the production of these preparations.

The present invention also includes pharmaceutical preparations in dosage units. This means that the preparations are in the form of individual parts, for example tablets, dragees, capsules, pills, suppositories and ampoules, of which the content of active substance corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

Non-toxic, inert pharmaceutically suitable excipients are taken to mean solid, semisolid or liquid diluents, fillers and formulation auxiliaries of all kinds.

Tablets, dragees, capsules, pills, granules, suppositories, solutions, suspensions and emulsions, pastes, ointments, gels, creams, lotions, powders and sprays may be mentioned as preferred pharmaceutical preparations.

Tablets, dragees, capsules, pills and granules can contain the active compound or compounds together with the customary excipients such as (a) fillers and extenders, for example starches, lactose, sucrose, glucose, mannitol and silica, (b) binders, for example carboxymethylcellulose, alginates, gelatin and polyvinylpyrrolidone, (c) humectants, for example glycerine, (d) disintegrating agents, for example agar-agar, calcium carbonate and sodium bicarbonate, (e) solution retarders, for example paraffin, and (f) resorption accelerators, for example quaternary ammonium compounds, (g) wetting agents, for example cetyl alcohol or glycerine monostearate, (h) adsorbents, for example kaolin and bentonite, and (i) lubricants, for example talc, calcium stearate and magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract optionally in a delayed manner, examples of embedding compositions which can be used being polymer substances and waxes.

The active compound or compounds, optionally together with one or more of the abovementioned excipients, can also be in a microencapsulated form.

Suppositories can contain, in addition to the active compound or compounds, the customary water-soluble or water-insoluble excipients, for example polyethylene glycols, fats, for example cocoa fat, and higher esters (for example $C_{14}$-alcohol with $C_{16}$-fatty acid) or mixtures of these substances.

Ointments, pastes, creams and gels can contain the customary excipients in addition to the active compound or compounds, for example animal and vegetable fats, waxes, paraffins, starch, tragacanth, cellulose derivatives, polyethylene glycols, silicones, bentonites, silica, talc and zinc oxide or mixtures of these substances.

Powders and sprays can contain the customary excipients in addition to the active compound or compounds, for example lactose, talc, silica, aluminium hydroxide, calcium silicate and polyamide powders or mixtures of these substances. Sprays can additionally contain the customary propellants, for example chlorofluorohydrocarbons.

Solutions and emulsions can contain the customary excipients in addition to the active compound or compounds, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerine, glycerine-formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain the customary excipients in addition to the active compound or compounds, such as liquid diluents, for example water, ethyl alcohol or propylene glycol, suspending agents, for example ethoxylated isostearyl alcohols, polyoxyethylene sorbitol esters and polyoxyethylene sorbitan esters, microcrystalline cellulose, aluminum metahydroxide, bentonite, aqar-agar and tragacanth, or mixtures of these substances.

The formulation forms mentioned can also contain dyestuffs, preservatives and additives which improve the odour and flavour, for example peppermint oil and eucalyptus oil and sweeteners, for example saccharin.

The therapeutically active compounds should preferably be present in the abovementioned pharmaceutical preparations in a concentration of about 0.1 to 99.5, preferably of about 0.5 to 95, % by weight of the total mixture.

The abovementioned pharmaceutical preparations can also contain other pharmaceutically active compounds in addition to the compounds according to the invention.

The abovementioned pharmaceutical preparations are manufactured in the usual manner according to known methods, for example by mixing the active compound or the active compounds with the excipient or excipients.

In humans and animals, the preparations mentioned can be administered either orally, rectally, parenterally (intravenously, intramuscularly or subcutaneously), intracisternally, intravaginally, intraperitoneally, locally (powder, ointment or drops) and for therapy of infections in cavities and body cavities. Suitable preparations are injection solutions, solutions and suspensions for oral therapy, gels, pour-on formulations, emulsions, ointments or drops. Ophthalmological and dermatological formulations, silver salts and other salts, ear drops, eye ointments, powders or solutions can be used for local therapy. In the case of animals, intake can also be effected in suitable formulations via the feed or drinking water. Furthermore, gels, oral powders, dusting powders, tablets, retard tablets, premixes, concentrates, granules, pellets, tablets, boli, capsules, aerosols, sprays and inhalants may be used in humans and animals. Furthermore, the compounds according to the invention can be incorporated into other excipient materials, such as, for example, plastics, (plastic chains for local therapy), collagen or bone cement.

In general, it has proved advantageous, both in human medicine and veterinary medicine, to administer the active compound or compounds in total amounts of about 0.5 to about 500, preferably 5 to 100 mg/kg of body weight every 24 hours, if appropriate in the form of several individual administrations, in order to achieve the desired results. An individual administration contains the active compound or compounds according to the invention preferably in amounts of about 1 to about 80, particularly 3 to 30, mg/kg of body weight. However, it may be necessary to deviate from the dosages mentioned and in particular to do so as a function of the nature and the body weight of the subject to be treated, the nature and severity of the disorder, the nature of the preparation and of the administration of the medicament, and the time or interval over which the administration takes place.

Thus, it may suffice, in some cases, to manage with less than the abovementioned amount of active compound, whilst in other cases the abovementioned amount of active compound must be exceeded. The particular optimum dosage required and the type of administration of the active compounds can easily be decided by anyone skilled in the art, on the basis of his expert knowledge.

The new compounds can be administered, in the usual concentrations and preparations, together with the feedstuff or the feedstuff preparations, or with the drinking water. This permits infection by Gram-negative or Gram-positive bacteria to be prevented, ameliorated and/or healed, and thereby allows promotion of growth and improved utilization of the feedstuff to be achieved.

PREPARATION EXAMPLES

Example 1

7 β-[2-(5-Amino-1,2,4-thiadiazol-3-yl)-2-(Z)-methoxyiminoacetamido]-3-(4-aminocarbonyl-1-methylpiperazinium)-methyl-cephem-4-carboxylate hydrosulphate

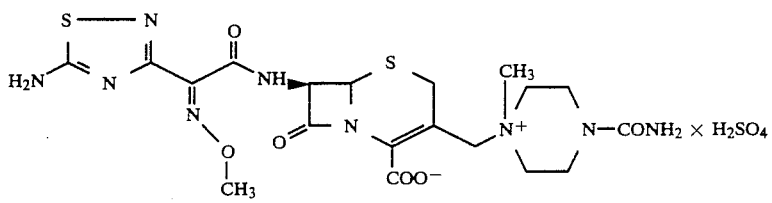

3.0 g (14.8 mmol) of 2-(5-amino-1,2,4-thiadiazol-3-yl)-2-(Z)-methoxyiminoacetic acid are dissolved in 30 ml of absolute dimethylformamide at room temperature under a nitrogen atmosphere. 4 ml of a 1:2 molar mixture of N-ethyldiiso-propylamine and tributylamine are added at $-50°$ C. 1.1 ml (14.2 mmol) of methanesulphonyl chloride are added, and the solution is stirred for 30 minutes at $-50°$ C. This solution is subsequently added rapidly to a solution, cooled to $0°$ C., of 3.0 g (6.6 mmol) of 7-amino-3-(4-aminocarbonyl-methylpiperazinium)-methyl-3-cephem-4-carboxylate (x $H_2SO_4$) in 10 ml of water and 5 ml of triethylamine. After 15 minutes, the reaction solution is transferred into 1.0 liters of acetone. The precipitate produced is filtered off under suction and dried. For purification, the sulphate is prepared, which is produced in a yield of 1.27 g.

$^1$H NMR (DCOOD): $\delta = 6.13$ [1]d; 5.55 [1]d; 5.12 [1]bd; 4.56 [1]bd, 4.3—4.1 [4]bd+s; 4.03 [1]bd, 3.88—3.57 [8]m, 3.43 [3]s ppm.

$^{13}$C NMR (DCOOD): $\delta = 182.36$ (C-5''); 167.47; 166.35; 163.04; 162.73 (C-1'', C-8, C-9, C-4'''); 153m43 (C-3); 143.90 (C-2''); 136.55 (C-4); 121.07 (C-3); 70.17 (C-3'); 68.04 (NOCH$_3$); 63.16; 62.96 (C-2''); 62–69 (C-7); 61.88 (C-6); 48.69 (N—CH$_3$); 41.04 (C-3'''); 33.30 (C-2).

Example 2

7 β-[2-(5-amino-1,2,4-thiadiazol-3-yl)-2-(Z)-ethoxyiminoacetamido]-3-(4-aminocarbonyl-1-methyl-piperazinium)-methyl-3-cephem-4-carboxylate

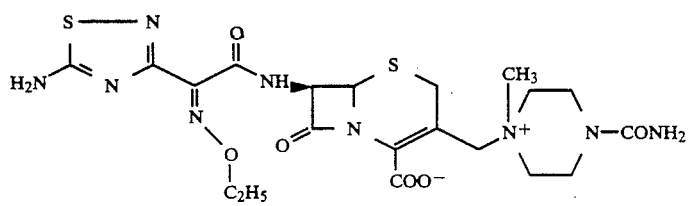

2.16 g (10 mmol) of 2-(5-amino-1,2,4-thiadiazol-3-yl)-(Z)-ethoxyiminoacetic acid are dissolved in 20 ml of absolute dimethylformamide at room temperature under a nitrogen atmosphere. After addition of 2.7 ml (10 mmol) of tributylamine, the mixture is cooled to $-50°$ C. 773 μl (10 mmol) of methanesulphonyl chloride are added, and the solution is stirred at $-50°$ C. for 30 minutes. This solution is subsequently added rapidly to a solution, cooled to $0°$ C., of 2.3 g (5 mmol) of 7-amino-3-(4-aminocarbonyl-1-methylpiperazinium)-methyl-3-cephem-4-carboxylate (x $H_2SO_4$) in 6.7 ml of water and 3.4 ml of triethylamine. After 15 minutes, the reaction solution is transferred into 1 liter of acetone. The resultant precipitate is filtered off under suction, dried and chromatographed over adsorber resin HP-20 (eluent: $H_2O$ to $H_2O$/acetone 80/20, v/v). Yield: 770 mg $^1$H NMR (DCOOD): $\delta = 6.10$ [1]d; 5.50 [1]d; 5.09 [1]bd; 4.50 [1]bd; 4.49 [2]q; 4.5–3.63 [12]m; 3.38 [3]s; 1.40 [3]t ppm.

Example 3

7 β-[2-(5-Amino-1,2,4-thiadiazol-3-yl)-2-(Z)-propyloxyiminoacetamido]-3-(4-aminocarbonyl-1-methyl-piperazinium)-methyl-3-cephem-4-carboxylate

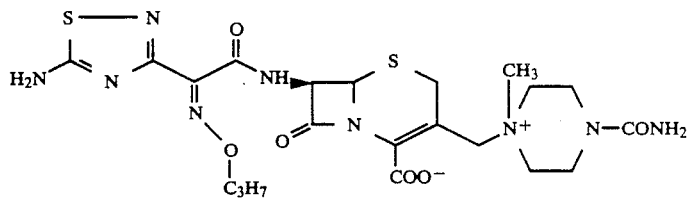

1.72 g (7.5 mmol) of 2-(5-amino-1,2,4-thiadiazol-3-yl)-2-(Z)-propyloxyiminoacetic acid are reacted, as described for example 2, with 2.3 g (5 mmol) of 7-amino-3-(4-aminocarbonyl-1-methylpiperazinium)methyl-3-cephem-4-carboxylate (x $H_2SO_4$) to give 720 mg of product.

$^1$H NMR (DCOOD): $\delta = 6.09$ [1]d; 5.50 [1]d, 5.08 [1]bd, 4.48 [1]bd; 4.38 [2]t; 4.25–3.60 [10]m; 3.38 [3]s; 1.80 [2]sex.; 0.95 [3]t ppm.

Example 4

7 β-[2-(5-Amino-1,2,4-thiadiazol-3-yl)-2-(Z)-butyloxyiminoacetamido]-3-(4-aminocarbonyl-1-methyl-piperazinium)-methyl-3-cephem-4-carboxylate

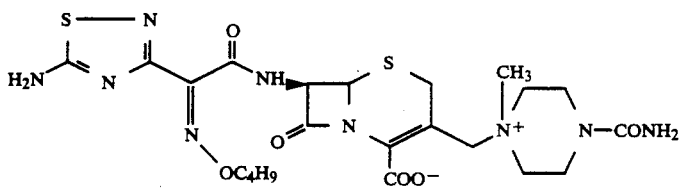

4.3 g (17.6 mmol) of 2-(5-amino-1,2,4-thiadiazol-3-yl)-2-(Z)-butyloxyiminoacetic acid are reacted, as described in Example 2, with 5.4 g (11.7 mmol) of 7-amino-3-(4-aminocarbonyl-1-methylpiperazinium)-methyl-3-cephem-4-carboxylate (x H₂SO₄) to give 1.55 g of product.

¹H NMR (DCOOD), δ=6.08 [1]d; 5.48 [1]d; 5.08 [1]bd; 4.48 [1]bd; 4.41 [2]t; 4.25–3.63 [10]m; 3.36 [3]s; 1.75 [2]quin.; 1.40 [2]sex; 1.90 [3]t ppm.

Example 5

7 β-[2-(5-Amino-1,2,4-thiadiazol-3-yl)-2-(Z)-allyloxyiminoacetamido]-3-(4-aminocarbonyl-1-methylpiperazinium)-methyl-3-cephem-4-carboxylate

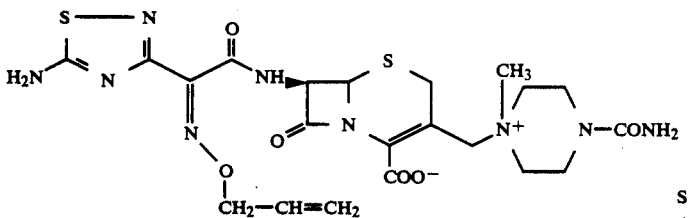

3 44 g (15 mmol) of 2-(5-amino-1,2,4-thiadiazol-yl)-2-(Z)-allyloxyiminoacetic acid are reacted, as described in Example 2, with 3.4 g (7.5 mmol) of 7-amino-3-(4-aminocarbonyl-1-methylpiperazinium)methyl-3-cephem-4-carboxylate (x H₂SO₄) to give 700 mg of product.

¹H NMR (DCOOD): δ=6.06 [1]d; 5.45 [1]d; 5.30 [1]bd; 5.06–4.75 [2]m; 4.47 [1]bd; 4.25–3.55 [4]m, 3.38–3.13 [13]m ppm.

Example 6

7 β-[2-(5-Amino-1,2,4-thiadiazol-3-yl)-2-(Z)-cyclopentyloxyacetamido]-3-(4-aminocarbonyl-1-methyl-piperazinium)-methyl-3-cephem-4-carboxylate

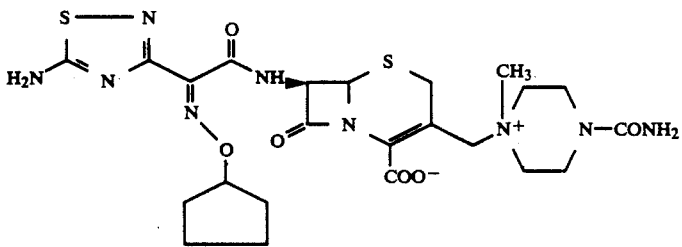

3.3 g (12.9 mmol) of 2-(5-amino-1,2,4-thiadiazol-yl)-2-(Z)-cyclopentyloxyiminoacetic acid are reacted, as described in Example 2, with 3.0 g (6.5 mmol) of 7-amino-3-(4-aminocarbonyl-1-methylpiperazinium)methyl-3-cephem-4-carboxylate (x H₂SO₄) to give 770 mg of product.

¹H NMR (DCOOD): δ=6.08 [1]d; 5.49 [1]d; 5.08 [1]bd; 5.00 [1]quin; 4.48 [1]bd; 4.3–3.6 [10]m; 3.38 [3]s; 2.0–1.5 [8]m ppm.

It is understood that the specification and examples are illustrative but not limitative of the present invention and that other embodiments within the spirit and scope of the invention will suggest themselves to those skilled in the art.

I claim:

1. A cephalosporin derivative of the formula (I)

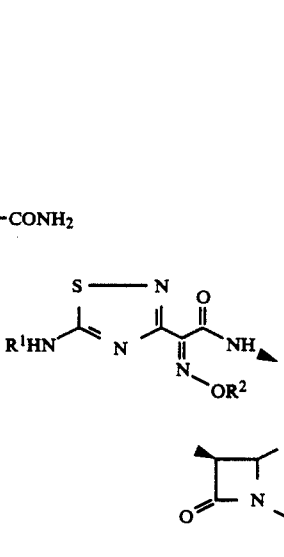

in which
R¹ represents hydrogen or an amino-protecting group 4-methoxyphenyl, 4-methoxymethyloxyphenyl, 4-[(2-methoxyethoxy) methyloxy]phenyl, 3,4-dimethoxyphenyl, benzyl, 2-nitrobenzyl, 4-nitrobenzyl, 4-methoxybenzyl, 2,4-dimethoxybenzyl, 3,4-dimethoxybenzyl, 2,4,6-trimethoxybenzyl, vinyl, allyl, tert-butoxycarbonyl, benzyloxycarbonyl, 2-nitrobenzyloxycarbonyl, 4-nitrobenzyloxycarbonyl, formyl, acetyl, chloroacetyl trichloroacetyl, trifluoroacetyl, benzoyl, methoxycarbonyl, allyloxycarbonyl, 2,4dimethoxybenzyloxycarbonyl, 2,2-diethoxyethyl, methoxycarbonylmethyl, tert-butoxycarbonylmethyl, allyloxymethyl, benzoylmethyl, bis-(4-methoxyphenyl)methyl, methoxymethyl, methylthiomethyl, methoxyethoxymethyl, 2-(methylthiomethyoxy)ethoxycarbonyl, 2hydroxy-2-phenylmethylmethoxy-(4-methoxyphenyl)methyl, trimethyl-, triethy and triphenylsilyl, tert-butyl-dimethylsilyl, tert-butyl-diphenylsilyl and [2-(trimethylsilyl)ethoxy]-methyl
and
$R^2$ represents alkyl, of 1 to 12 carbon atoms cycloalkyl of up to 12 carbon atoms or alkenyl of 2 to 12 carbon atoms.

2. A cephalosporin derivative according to claim 1, in which
$R^1$ represents hydrogen or acetyl and
$R^2$ represents straight-chain or branched alkyl having up to 8 carbon atoms, or represents cyclopropyl, cyclopentyl or cyclohexyl or
represents straight-chain or branched alkenyl having up to 8 carbon atoms and one or two double bonds.

3. A cephalosporin derivative according to claim 1, in which
$R^1$ represents hydrogen and
$R^2$ represents straight-chain or branched alkyl having up to 6 carbon atoms, cyclopentyl, cyclohexyl or straight-chain or branched alkenyl having up to 4 carbon atoms and one double bond.

4. A cephalosporin derivative according to claim 1, in which $R^2$ represents methyl, ethyl, propyl, isopropyl, butyl, isobutyl, pentyl, isopentyl, hexyl, isohexyl, heptyl, isoheptyl, octyl, isooctyl, allyl, propenyl, isopropenyl, butenyl, isobutenyl, pentenyl, isopentenyl, hexenyl, isohexenyl, heptenyl, isoheptenyl, octenyl or isooctenyl.

5. A compound according to claim 1, wherein such compound is 7 β-[2-5-amino-1,2,4-thiadiazol-3-yl)-2-(Z)-methoxyiminoacetamido]-3-(4-aminocarbonyl-1-methylpiperazinium)-methyl-3-cephem-4-carboxylate of the formula

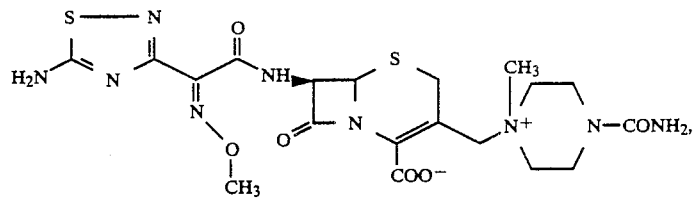

or a physiologically acceptable salt thereof.

6. A compound according to claim 1, wherein such compound is 7 β-[2-(5-amino-1,2,4-thiadiazol-3-yl)-2-(Z)-ethoxyimino-acetamido]-3-(4-aminocarbonyl-1-methylpiperazinium)-methyl-3-cephem-4-carboxylate of the formula

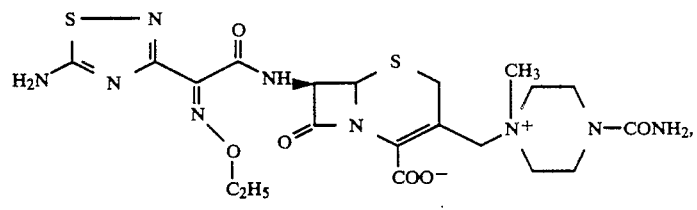

or a physiologically acceptable salt thereof

7. A compound according to claim 1, wherein such compound is 7 β-[2-(5-amino-1,2,4-thiadiazol-3-yl)-2-(Z)-propyloxy-iminoacetamido]-3-(4-aminocarbonyl-1-methylpiperazinium)-methyl-3-cephem-4-carboxylate of the formula

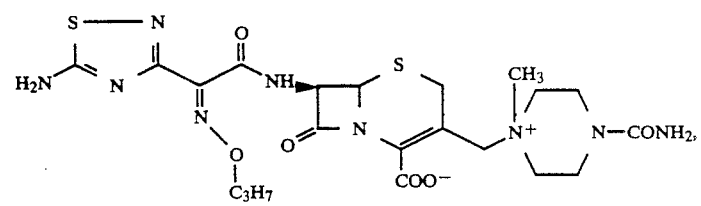

or a physiologically acceptable salt thereof.

8. A compound according to claim 1, wherein such compound is 7 β-[2-(5-amino-1,2,4-thiadiazol-3-yl)-2-(Z)-butyloxy-iminoacetamido]3-(4-aminocarbonyl-1-methyl-piperazinium)-methyl-3-cephem-4-carboxylate of the formula

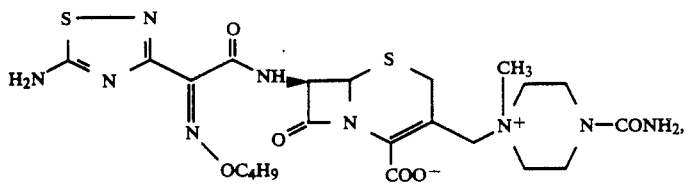

a physiologically acceptable salt thereof

9. A compound according to claim 1, wherein such compound is 7 β-[2-(5-amino-1,2,4-thiadiazol-3-yl)-2-(Z)-allyloxyimino-acetamido]-3-(4-aminocarbonyl-1-methyl-piperazinium)-methyl-3-cephem-4-carboxylate of the formula

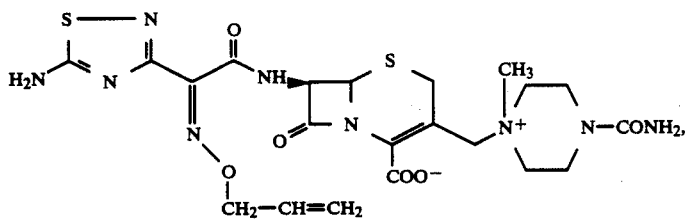

or a physiologically acceptable salt thereof.

10. A compound according to claim 1, wherein such compound is 7 β-[2-(5-amino-1,2,4-thiadiazol-3-yl)-2-(Z)-cyclopentyl-oxyacetamino]-3-(4-aminocarbonyl-1-methylpiperazinium)-methyl-3-cephem-4-carboxylate of the formula

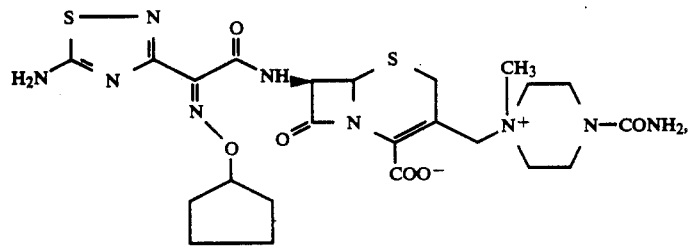

a physiologically acceptable salt thereof.

11. An antibacterial composition comprising an antibacterially effective amount of a compound or salt according to claim 1 and a pharmacologically acceptable diluent.

12. A method of combating bacterial infection in a patient in need thereof which comprises administering to such patient an antibacterially effective amount of a compound or salt according to claim 1.

13. The method according to claim 12, wherein such compound is

7 β-[2-5-amino-1,2,4-thiadiazol-3-yl)-2-(Z)-methoxyimino-acetamido]-3-(4-aminocarbonyl-1-methyl-piperazinium)-methyl-3-cephem-4-carboxylate, 7 β[2-(5-amino-1,2,4-thiadiazol-3-yl)-2-(Z)-ethoxyimino-acetamido]-3-(4-aminocarbonyl-1-methyl-piperazinium)-methyl-3-cephem-4-carboxylate, 7 β-[2-(5-amino-1,2,4-thiadiazol-3-yl)-2-(Z)-propyloxy-iminoacetamidol]-3-(4-aminocarbonyl-1-methyl-piperazinium)-methyl-3-cephem-4-carboxylate, 7 β-[2-(5-amino-1,2,4-thiadiazol-3-yl)-2-(Z)-buytloxy-iminoacetamido]-3-(4-aminocarbonyl-1-methyl-piperazinium)-methyl-3-cephem-4-carboxylate or 7 β-[2-(5-amino-1,2,4-thiadiazol)-3-yl)-2-(Z)-allyloxyimino-acetamido]-3-(4-aminocarbonyl-1-methyl-piperazinium)-methyl-3-cephem-4-carboxylate, or a physiologically acceptable salt thereof.

14. A method of combating a Pseudomonas bacterial infection in a patient which comprises administering to such patient an antibacterially effective amount of a compound or salt according to claim 1.